United States Patent [19]

Sawai et al.

[11] Patent Number: 5,059,594

[45] Date of Patent: Oct. 22, 1991

[54] PHYTIC ACID COMPOSITIONS

[75] Inventors: Kiichi Sawai, Funabashi; Masayasu Kurono, Mie; Hiromoto Asai, Nagoya; Takahiko Mitani, Mie; Naohisa Ninomiya, Nagoya; Tomoo Suzuki, Kasugai, all of Japan

[73] Assignee: Sanwa Kagaku Kenkyusho Co., Ltd., Nagoya, Japan

[21] Appl. No.: 497,364

[22] Filed: Mar. 22, 1990

[30] Foreign Application Priority Data

Mar. 31, 1989 [JP] Japan .................................... 1-82599

[51] Int. Cl.$^5$ ............................................. A61K 31/66
[52] U.S. Cl. .................................................. 514/103
[58] Field of Search ................................. 514/121, 103

Primary Examiner—Frederick E. Waddell
Assistant Examiner—Diane Gardmer
Attorney, Agent, or Firm—Armstrong, Nikaido, Marmelstein, Kubovcik & Murray

[57] ABSTRACT

A novel composition contains phytic acid and ferric ions as main ingredients and carboxylic acid ions as a dissolution accelerator, and may further include at least one or more or two additives selected from the group consisting of a carboxylic acid or its salt, saccharides, an amino acid or its salt and an organic phosphoric acid or its salt.

4 Claims, 4 Drawing Sheets

o——o Present composition
F Administration of present composition
x——x Control
←D→ Administration of Alcohol

○——○ Present composition
F  Administration of present composition
×——× Control
◆—□—◆ Administration of Alcohol

PHYTIC ACID COMPOSITIONS

BACKGROUND OF THE INVENTION

1. Field of the Invention

The present invention relates to a novel highly water-soluble composition containing as primary ingredients phytic acid and ferric ions and as a dissolution accelerator carboxylic acid ions and further including as an additive a carboxylic acid or its salt, a saccharide, an amino acid or its salt and an organic phosphoric acid compound or its salt. The present invention is also concerned with the use of such a composition, e.g., pharmaceutical preparations making use of its effects upon the removal of uraroma and body smell, detoxication, the treatment of diabetes and hyperlipemia, the remediation of erythrocyte flexibility and dysmnesia and the inhibition of the proliferation of fat cells.

2. Prior Art

Phytic acid is a hexaphosphate of inositol, and occurs naturally in various kinds of plants in the form of mixed combined salts (Phytin) with calcium, magnesium and potassium.

Phytic acid and its salts have already been used as pharmaceuticals. For instance, calcium phytate has been used as calcium enhancers; sodium phytate for the prevention of the recurrence of calculus; potassium phytate for the treatement of hypercalcemia; and so on.

In the form of food additives, phytic acid has also been used to prevent the blackening of canned foods and the formation of strabite therein, prevent the discoloration of fruit juice and drinking water, promote fermentation and prevent the oxidation of edible oils as well as for other purposes.

In addition, the oral administration of phytic acid has been effective for the removal of uraroma and body smell, detoxication, the treatment of diabetes and hyperlipemia, the remediation of erythrocyte flexibility, dysmnesia and hypohepatia and the inhibition of the proliferation of fat cells. Further studies made by the present inventors have revealed that such functions are further enhanced by the addition of ferric ions to phytic acid.

It has been found, on the other hand, that the administration of phytic acid gives rise to a lowering of the absorption of metal ions simultaneously with a metal deficiency, because phytic acid bonds to metal ions such as $Ca^{2+}$, $Zn^{2+}$, $Fe^{2+}$ and $Fe^{3+}$ to form insoluble chelates and salts—see Eiji MIYAZAWA and Tsutomu YOSHIDA, "The Progress in Medical Science", Vol. 144, No. 10 (1988).

It has also been known in the case of a heavy metal salt formed of phytic acid and ferric chloride, such as monoferric phytate, a heavy metal of five or more equivalents bonds to a part of phytic acid to form an insoluble heavy metal salt—see Japanese Patent Publication No. 43(1968)-16977. Further, it has been known that diferric or tetraferric phytate obtained from phytic acid and a ferric salt is lower in bioavailability than monoferric phytate—see Lipschitz D. A. et al, "J. Nutr.", 109, page 1154 (1979).

Thus, a primary object of the present invention is to provide a ferric salt of phytic acid which does not bring about a lowering of the bioabsorption of ferric ions that is the defect of phytic acid, and is of solubility so high that its bioavailability can be high.

According to the present invention, the above object is achieved by the provision of a novel composition of phytic acid, in which ferric ions are rather positively supplemented to phytic acid, and carboxylic acid ions as a dissolution accelerator and other additives are further added to enhance the bioabsorption of phytic acid and ferric ions.

BRIEF DESCRIPTION OF THE DRAWINGS

The present invention will now be explained in detail with reference to the accompanying drawings, which are provided for the purpose of illustration alone and in which:

FIG. 1 is graphical views showing changes-with-time of ethanol, acetaldehyde, total keton body and blood sugar value in the blood of rabbits when phytic acid and the present composition are administrated to the rabbits with ethanol, FIG. 1(a) showing the results of the administration of phytic acid alone and FIG. 1(b) the results of the administration of the present composition, and FIGS. 2-4 are graphical views showing the results of pulse frequency changes, flash, sleep inducing and intoxication/dizziness, when the present composition is administered before, just after and 30 minutes after drinking, FIGS. 2(a), (b), (c) and (d) slow the results before drinking, FIGS. 3(a), (b), (c), and (d) the results after just drinking and FIGS. 4(a), (b), (c) and (d) the results 30 minutes after drinking.

DETAILED DESCRIPTION OF THE INVENTION

The carboxylic acid ions used as the dissolution accelerator in the present invention refer to ions of monobasic acids such as acetic acid, propionic acid and lactic acid and polybasic acids such as maloic acid, succinic acid, fumaric acid, maleic acid, malic acid, tartaric acid and citric acid.

The "other additives" may refer to, for instance, a carboxylic acid or its salt, a saccharide, an amino acid or its salt and an organic phosphoric acid compound or its salt.

The carboxylic acids or their salts used as the additives may include monobasic acids such as acetic acid, propionic acid and lactic acid and polybasic acids such as maloic acid, succinic acid, fumaric acid, maleic acid, malic acid, tartaric acid and citric acid as well as their sodium, potassium, calcium and ammonium salts.

The saccharidies used as the additives may include monosaccharides such as glucose, galactose, sorbitol and glucuronic acid; disaccharides such as sucrose and lactose; oligosaccharides such as water-soluble dextrin; and polysaccharides such as starch.

The amino acids or their salts used as the additives may include chargeless amino acids such as glycine, alanine and serine; basic amino acids such as lysine and arginine; acidic amino acids such as aspartic acid and glutamic acid; and their salts such as sodium salts, potassium salts, calcium salts, ammonium salts, hydrochlorates and hydrobromates.

The phosphoric acid compounds or their salts used as the additives may include phosphoserine and glycerophsphate or their salts such as sodium, potassium, calcium and ammonium salts.

In the novel compositions according to the present invention, the molar ratio of phytic acid:ferric ions:carboxylic acid ions as the dissolution accelerator: additives is generally about 10:1:1:0 to about 1:12:36:200. The concentration of phytic acid is then suitable in a range of about 1.00 mmol/l to about 1.00 mol/l.

More specifically, it is suitable that the molar ratio of phytic acid:ferric ions:citric acid ions as the dissolution accelerator is in a range of about 1:1:1 to about 1:4:4; the molar ratio of phytic acid:ferric ions:citric acid ions as the dissolution accelerator: citric acid or its sodium salt as the additive in a range of about 1:1:1:1 to about 1:4:4:128; the molar ratio of phytic acid:ferric ions:citric acid ions as the dissolution accelerator: glucose as the additive in a range of about 1:1:1:0 to about 1:2:2:128; the molar ratio of phytic acid:ferric ions:citric acid ions as the dissolution accelerator: water-soluble dextrine as the additive in a range of about 1:1:1:0 to about 1:2:2:8; the molar ratio of phytic acid:ferric ions:citric acid ions as the dissolution accelerator:lysine or its hydrochlorate as the additive in a range of about 1:0.5:0.5:0 to about 1:4:4:8; the molar ratio of phytic acid:ferric ions:citric acid ions as the dissolution accelerator: sodium glutamate as the additive in a range of about 1:1:1:0 to about 1:4:4:64; the molar ratio of phytic acid:ferric ions:citric acid ions as the dissolution accelerator: phosphoserine as the additive in a range of about 1:0.1:0.1:0 to about 1:1:1:2; and the molar ratio of phytic acid:ferric ions:citric acid ions as the dissolution accelerator: glycerophosphate as the additive in a range of about 1:1:1:0 to about 1:4:4:8. In these examples, the concentration of phytic acid is suitably in a range of about 5.00 mmol/l to about 50.0 mmol/l.

The novel composition according to the present invention may be prepared by preparing an aqueous solution containing, for instance, ferric ions and carboxylic acid ions such as citric acid ions and adding it to a predetermined concentration of phytic acid or a solution of a predetermined concentration of phyitic acid with additives.

The thus prepared compositions may be formulated into capsules, lemonade preparations, drinkable preparations and the like in conventional manners.

Although varying depending upon the purposes and preparations, the present compositions may be administrated to human beings, generally to adults, at a dose of 1 to 500 mg, calculated as phytic acid.

According to the present invention, the ferric salt of phytic acid whose solubility and bioavailability are increased without bringing about any in vivo absorption of ferric ions is obtained by adding to phytic acid and ferric ions carboxylic acid ions as a dissolution accelerator and additives such as carboxylic acids or their salts, saccharides, amino acids or their salts, organic phosphoric acid compounds or their salts.

Thus, the compositions of the present invention produce an increased action upon the removal of uraroma and body smell, detoxication, the treatment of diabetes and hyperlipemia, the remediation of erythrocyte flexibility, dysmnesia and hypohepatia and the inhibition of the proliferation of fat cells.

EXAMPLES

The present invention will now be explained in more detail with reference to the examples including preparative examples and experiments.

REFERENCE EXAMPLE 0.200 ml/l of Aqueous Solution of Ferric Citrate

Dissolved in refined water were 16.2 g (60.0 mmol) of ferric chloride.$6H_2O$ and 17.6 g (60.0 mmol) of sodium citrate.$2H_2O$ to obtain 300 ml of an aqueous solution that is an aqueous solution of 0.200 mol/l of ferric citrate (pH 1.73).

EXAMPLE 1

Under agitation, 0.302 ml (0.0604 mmol) of 0.200 mol/l of an aqueous solution of ferric citrate are added dropwise to 20.0 ml (0.0302 mmol) of 1.51 mmol/l of phytic acid to form a colorless, transparent solution (pH 2.49).

EXAMPLE 2

Under agitation, 1.00 ml (0.200 mmol) of 0.200 mol/l of an aqueous solution of ferric citrate are added dropwise to 20.0 ml (0.100 mmol) of 5.00 mmol/l of phytic acid to form a colorless, transparent solution (pH 2.19).

EXAMPLE 3

Under agitation, 1.51 ml (0.302 mmol) of 0.200 mol/l of an aqueous solution of ferric citrate are added dropwise to 20.0 ml (0.302 mmol) of 15.1 mmol/l of phytic acid to form a pale yellow, transparent solution (pH 1.78).

EXAMPLE 4

Added to 20.0 ml (0.302 mmol) of 15.1 mmol/l of phytic acid are 508 mg (2.42 mmol) of citric acid.$H_2O$, and 1.51 ml (0.302 mmol) of 0.200 mol/l of an aqueous solution of phytic acid are added dropwise under agitation to the resulting solution to form a pale yellow, transparent solution (pH 1.70).

EXAMPLE 5

Added to 20.0 ml (0.302 mmol) of 15.1 mmol/l of phytic acid are 711 mg (2.42 mmol) of trisodium citrate.$2H_2O$, and 6.04 ml (1.21 mmol) of 0.200 mol/l of an aqueous solution of phytic acid are added dropwise under agitation to the resulting solution to form a pale yellow, transparent solution (pH 4.47).

EXAMPLE 6

Added to 20.0 ml (0.302 mmol) of 15.1 mmol/l of phytic acid are 54.4 mg (0.302 mmol) of glucose, and 1.51 ml (0.302 mmol) of 0.200 mol/l of an aqueous solution of phytic acid are added dropwise under agitation to the resulting solution to form a pale yellow, transparent solution (pH 1.78).

EXAMPLE 7

Added to 20.0 ml (0.302 mmol) of 15.1 mmol/l of phytic acid are 498 mg of water-soluble dextrin, and 1.51 ml (0.302 mmol) of 0.200 mol/l of an aqueous solution of phytic acid are added dropwise under agitation to the resulting solution to form a pale yellow, transparent solution (pH 1.77).

EXAMPLE 8

Added to 20.0 ml (0.302 mmol) of 15.1 mmol/l of phytic acid are 353 mg of L-lysine (2.42 mmol), and 3.03 ml (0.604 mmol) of 0.200 mol/l of an aqueous solution of phytic acid are added dropwise under agitation to the resulting solution to form a pale yellow, transparent solution (pH 4.53).

EXAMPLE 9

Added to 20.0 ml (0.302 mmol) of 15.1 mmol/l of phytic acid are 55.2 mg (0.302 mmol) of L-lysine monohydrochlorate, and 1.51 ml (0.302 mmol) of 0.200 mol/l of an aqueous solution of phytic acid are added dropwise under agitation to the resulting solution to form a pale yellow, transparent solution (pH 1.91).

EXAMPLE 10

Added to 20.0 ml (0.302 mmol) of 15.1 mmol/l of phytic acid are 452 mg (2.42 mmol) of sodium L-glutamate.$H_2O$, and 6.04 ml (1.21 mmol) of 0.200 mol/l of an aqueous solution of phytic acid are added dropwise under agitation to the resulting solution to form a yellow, transparent solution (pH 3.54).

EXAMPLE 11

Added to 20.0 ml (0.302 mmol) of 15.1 mmol/l of phytic acid are 55.9 mg of (0.302 mmol) of O-phospho-L-serine, and 0.755 ml (0.151 mmol) of 0.200 mol/l of an aqueous solution of phytic acid are added dropwise under agitation to the resulting solution to form a pale yellow, transparent solution (pH 1.72).

EXAMPLE 12

Added to 20.0 ml (0.302 mmol) of 15.1 mmol/l of phytic acid are 751 mg (2.42 mmol) of α-glycero-disodium phosphate.$H_2O$ (assay 69, 5%), and 6.04 ml (1.21 mmol) of 0.200 mol/l of an aqueous solution of phytic acid are added dropwise under agitation to the resulting solution to form a yellow, transparent solution (pH 3.59).

EXAMPLE 13

Composition A for Preparation

Lactose is added to the composition set forth in Ex. 1 (containing 200 mg of phytic acid), which is then dried to obtain 1000 mg of a powdery composition.

EXAMPLE 14

Composition B for Preparation

Lactose is added to the composition set forth in Ex. 8 (containing 200 mg of phytic acid), which is then dried to obtain 1000 mg of a powdery composition.

EXAMPLE 15

Composition C for Preparation

Purified water is added to the composition set forth in Ex. 2 (containing 100 mg of phytic acid) to obtain 1000 mg of a solution.

EXAMPLE 16

Example of Preparation—Capsule

| Composition A (containing 40 mg of phytic acid) | 200 mg |
|---|---|
| Lactose | 20 mg |
| Corn starch | 38 mg |
| Magnesium stearate | 2 mg |

The given amounts of the above ingredients are uniformly mixed together and packed in No. 2 capsules, each containing 40 mg of phytic acid.

EXAMPLE 17

Example of Preparation—Tablet

| Composition B (containing 20 mg of phytic acid) | 100 mg |
|---|---|
| Corn starch | 19 mg |
| Crystalline cellulose | 30 mg |
| Magnesium stearate | 1 mg |

The given amounts of the above ingredients are uniformly mixed together and compression-molded into tablets, each having a diameter of 7 mm, weighing 150 mg and containing 20 mg of phytic acid.

EXAMPLE 18

Example of Preparation—Lemonade

| Composition C (containing 30 mg of phytic acid) | 3 mg |
|---|---|
| Single syrup | 2.5 mg |
| Purified water Total amount | 30 mg |

The given amounts of the above ingredients are uniformly mixed together into lemonade preparations, which are administrated at a dose of 30 ml containing 300 mg of phytic acid.

EXAMPLE 19

Example of Preparation—Drinkable Preparation

| Composition C (containing 200 mg of phytic acid) | 2 g |
|---|---|
| Honey | 1 g |
| White sugar | 3 g |
| Citric acid | suitable amount |
| Sodium citrate | suitable amount |
| Peppermint | slight amount |
| Purified water | suitable amount |

The given amounts of the above ingredients are uniformly mixed together into an internal transparent liquid preparation, which is to be administrated at a dose of 50 ml containing 200 mg of phytic acid.

EXPERIMENT 1

Removal of Uraroma

To make rats discharge urine smelling like cat's urine, feed for cats having a high protein content (30%) was given thereto. That is, potassium phytate (3 mg/day, calculated as phytic acid) and the water-soluble composition of phytic acid and ferric citrate (3 mg/day, calculated as phytic acid) were intraperitoneally administrated to the first and second test groups of rats, respectively, over a period of five days, while no drug was given to a control group of rats, so as to investigate and compare uraroma.

The results are set forth in Table 1, from which it is found that uraroma is removed to a considerable extent in both the first and second test groups; this means that the present composition has a much stronger action upon the removal of uraroma.

TABLE 1

| | Uraroma | | | | | |
|---|---|---|---|---|---|---|
| | a | b | c | d | e | f |
| Control Group | ++ | ++ | ++ | ++ | ++ | ++ |
| Test Group 1 | ++ | + | ± | ± | ± | + |
| Test Group 2 | ++ | ± | − | − | ± | + | a: before administration, b: before 3 days, c: before 4 days, d: 5 days, e: 6 days and f: 9 days.

EXPERIMENT 2

Removal of Sweaty Smell

By having three volunteers suffering from the offensive smells of their feet and armpits—hircismus—and take one capsule set forth in Ex. 16 after every meal over a period of one week, three inspectors carried out daily response testing. Their stockings and shirts were extracted with a solvent to measure the amount of mercaptan contained. As a result, it was found that the amount of mercaptan tended to decrease with the lapse of time. The results of the response testing revealed that any offensive smell was substantially removed on the 7th day after administration.

EXPERIMENT 3

Detoxication of Alcohol

After white rabbits weighing about 3 kg (one for each group) had been fasted for 24 hours, 2 g/kg of alcohol was administered to the rabbits, and the concentrations of alcohol, acetaldehyde, ketone body and blood sugar in blood were measured with time. Further, the same rabbits were continuously and intraperitoneally provided with the present composition and phytic acid over a period of 6 days, each at a dose of 20 mg/kg, and were then fasted for 24 hours from the final administration to carry out similar tests as mentioned above. For measurement, blood was gathered from the auricular veins, and 3 mg/ml of sodium citrate were added to the blood for the separation of plasma, which was then examined with the following kits.

(a) Alcohol in Blood
F Kit for Ethanol (made by B. M. Yamanouchi).
(b) Acetaldehyde in Blood
F Kit For Acetaldehyde (made by Yamanouchi).
(c) Measurement of Ketone Body
Reagent Kit for Ketone Test (made by the applicant—Sanwa Chemical Co., Ltd.)
(d) Measurement of Blood Sugar Value
Glucose B-Test (made by Wako).

Figure 1A:
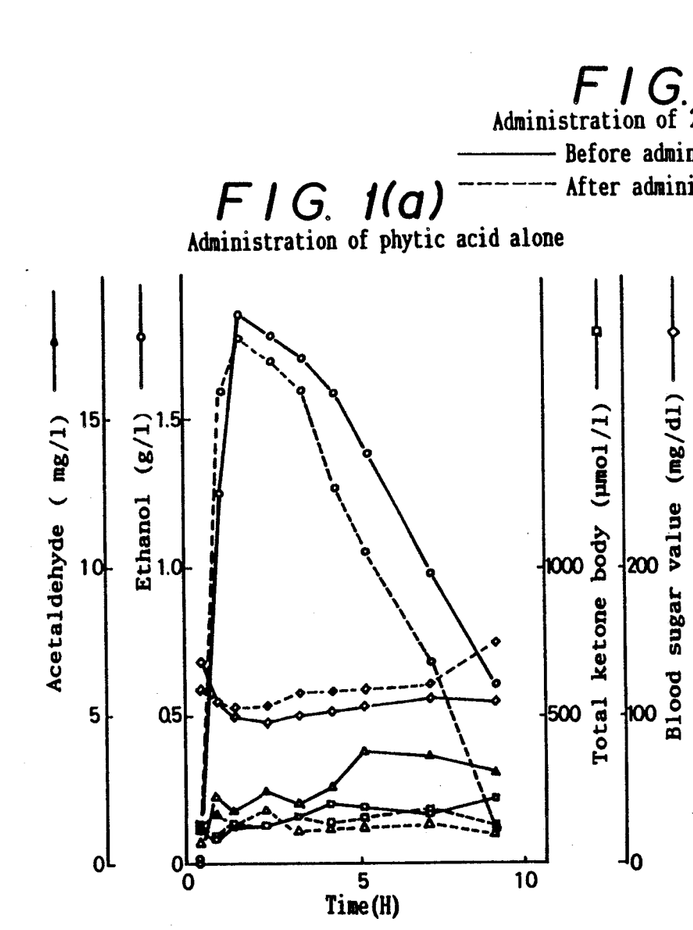
Figure 1B:
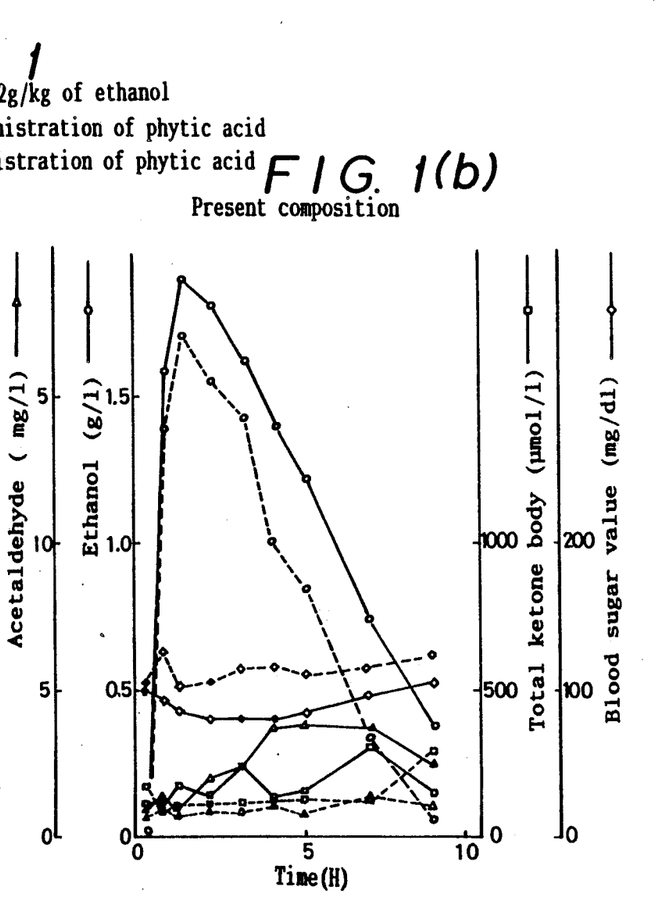

As shown in FIG. 1, it was revealed that the amounts of alcohol and acetaldehyde in blood were reduced by the administration of the present composition and phytic acid. On the other hand, no increase in the amount of ketone body was found within the blood gathering time. However, the amount of ketone body will certainly increase after alcohol disappears from blood. The blood sugar value was found to be slightly increased or not decreased by the administration of the present composition.

EXPERIMENT 4

Alcohol Response Testing

Figure 2A:
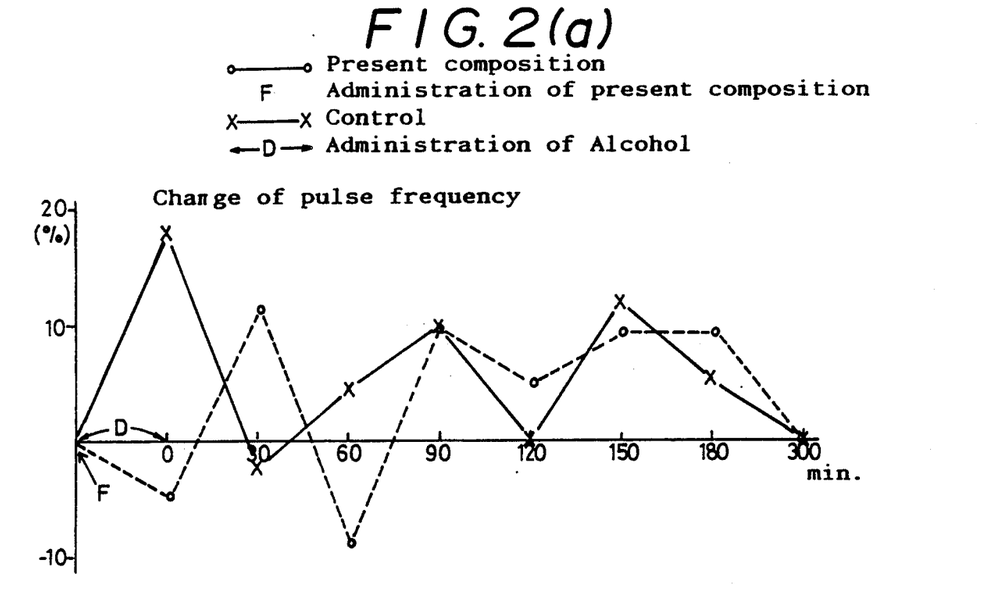
Figures 2B, 2C:
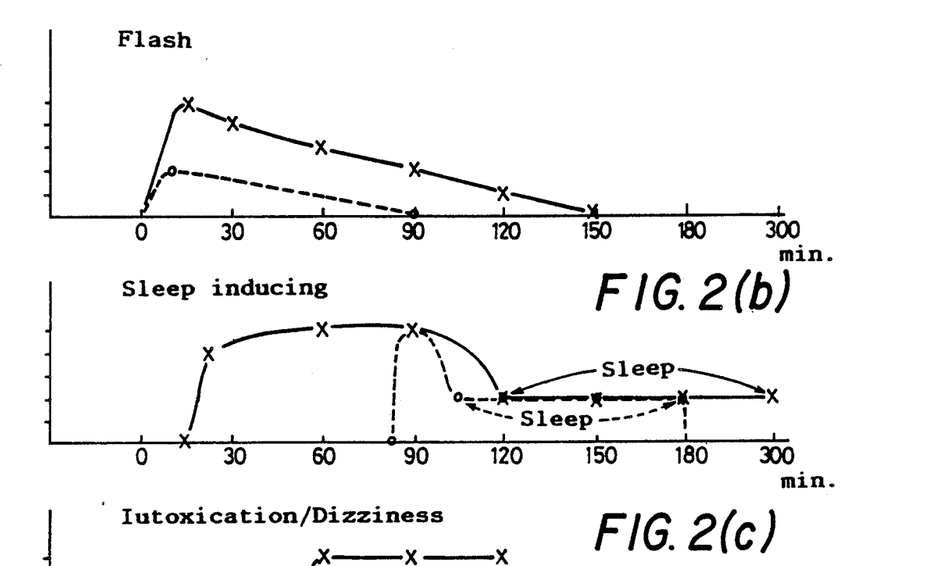
Figure 2D:
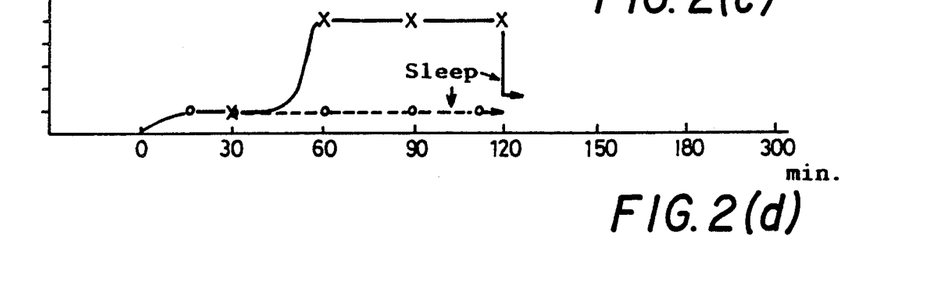
Figure 3A:
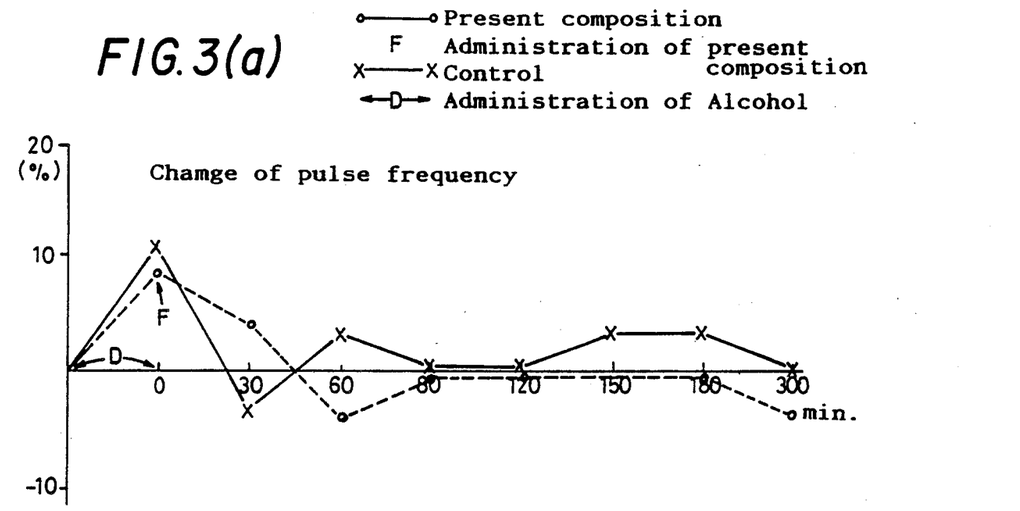
Figure 3B:
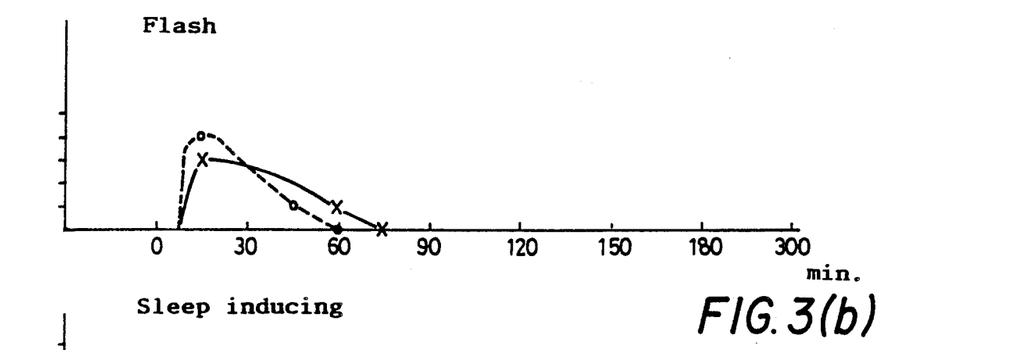
Figure 3C:
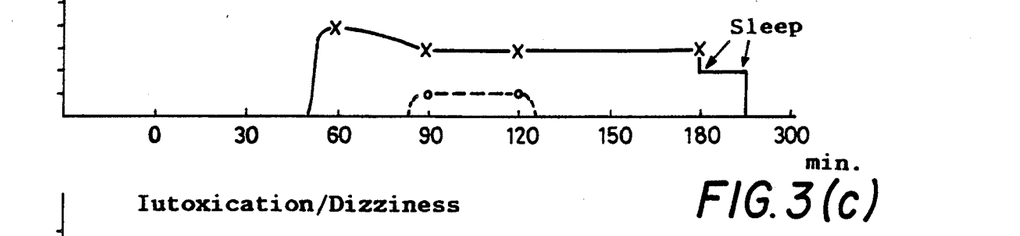
Figure 3D:
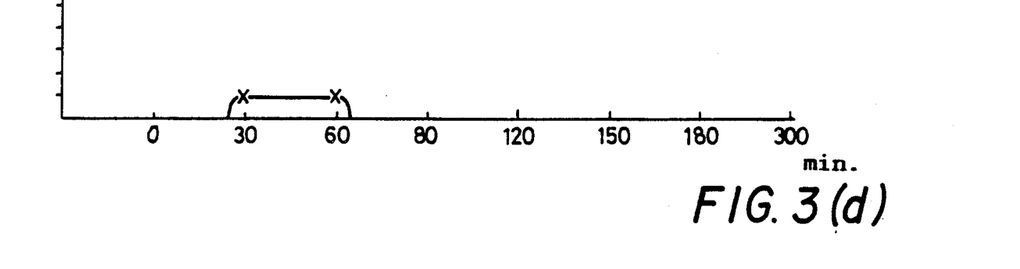
Figures 4A, 4B:
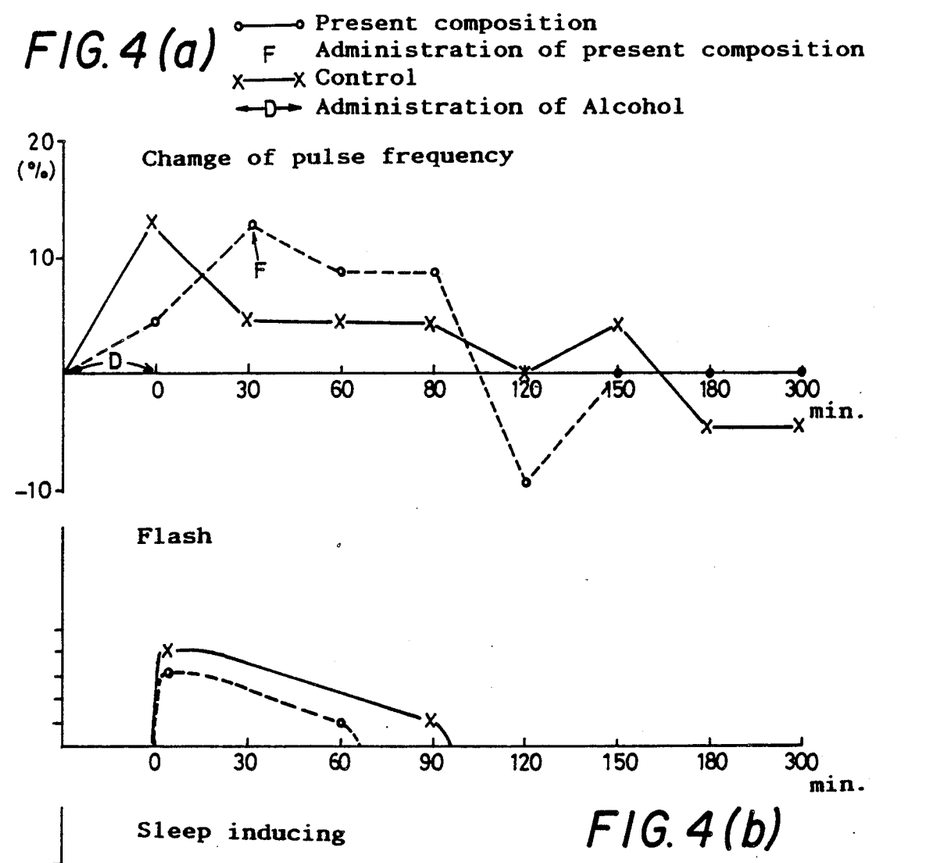
Figures 4C, 4D:
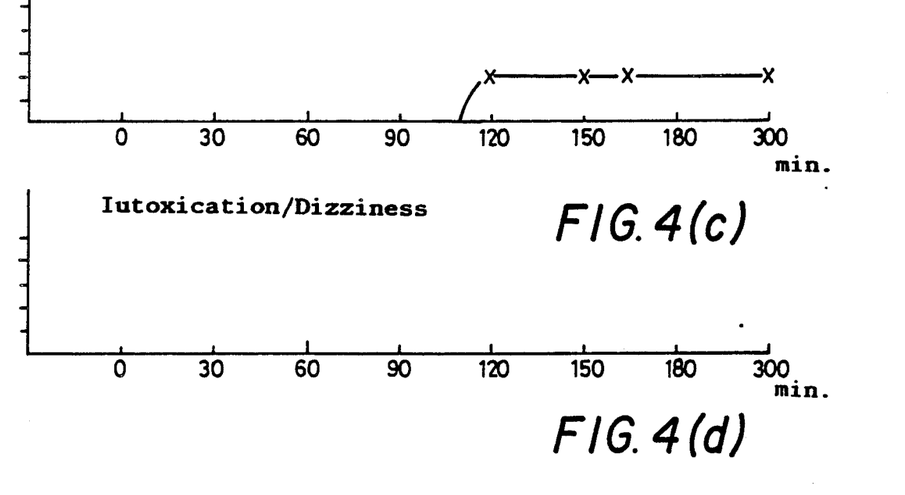

By having three groups of volunteers drink 360 cc of Sake on an empty stomach over 30 minutes and take one dose of the drinkable preparation of Ex. 19 before, just after and 30 minutes after drinking, investigations were made on the change of pulse frequency (%), the occurrence of flash (assayed by five ranks; this shall hold hereinafter), sleep inducing and intoxication. The results are shown in FIGS. 2–4 with the results of a control group in which the volunteers drunk Sake alone.

(A) Before Drinking (a) Change of Pulse Frequency
With alcohol alone, the pulse frequency showed a high at 0 minutes and dropped rapidly after 30 minutes. When the present composition was administered just after drinking, the pulse frequency was normal at 0 minutes, but accelerated after 30 minutes. In both cases, the pulse frequency contined to be increased but returned to normal after 300 minutes.
(b) Flash A difference in the degree of being intoxicated was reduced to half or less by the administration of the present composition.

(c) Sleep Inducing
With the administration of the present composition, the fumes of sleep were induced after the lapse of 80 minutes but disappeared after the lapse of 3 hours. In other words, it was found that the fumes of sleep were slowly induced and disappeared in a short time.

(d) Intoxication and Dizziness
With the administration of the present composition, the initial intoxication was sustained but slight.

(B) Just After Drinking (a) Change of Pulse Frequency
When the present composition was administered just after drinking, the change of pulse frequency was within a range of error. Just after the administration of the present composition, the pulse frequency dropped after about 30 minutes but immediately returned to normal.

(b) Flash
Taking physical condition or other factos into account, the degree of flash was within a range of error in both the groups. However, the time of flash was reduced to about 15 minutes in the test group.

(c) Sleep Inducing
In the test group, the fumes of sleep were not substantially induced.

(d) Intoxication and Dizziness
In the test group, neither intoxication nor dizziness was observed.

(C) 30 Minutes After Drinking (a) Change of Pulse Frequency
After the administration of the present composition, the pulse frequency was on a high level, but dropped rapidly after 90 minutes and then returned to normal. In the test group, the recovery time tends to be shortened.

(b) Flash
Taking the influences of physical condition, etc. into account, the degree of flash is within a range of error in both the groups. However, the time of flash is reduced to about 30 minutes in the test group.

(c) Sleep Inducing
In the test group, the fumes of sleep were not substantially induced.

(d) Intoxication and Dizziness
In both the groups, neither intoxication nor dizziness was observed.

Taken altogether, the present composition tends to have an effect of before drinking≧just after drinking≧30 minutes after drinking.

EXPERIMENT 5

Remediation of Drug Poisoning

Potassium phytate (5 mg/kg, calculated as phytic acid) and the present composition of Ex. 1 (5 mg/kg, calculated as phytic acid) were intraperitoneally administrated to test and control groups (1) and (2), six for each group, within 10 minutes after anesthetized by the intraperitoneal injection of 80 mg/kg of hexobarbital for the comparison of arousal time. As a result, a 30% or more reduction and a 35% or more reduction in the arousal time were found in the test groups (1) and (2), respectively. It is thus noted that the present composition is slightly stronger in action than potassium phytate.

EXPERIMENT 6

Action on the Suppression of Alloxan Diabetes

Used for testing were three groups of DDY male mice weighing about 20 g (21 to 23 g) and fasted for three hours, five per group. The testing control was intraperitoneally administrated with sodium phytate and the present composition (50 to 100 mg/kg, calculated as phytic acid), while the normal and control groups were dosed with physiological saline in an amount of 10 ml/kg. The control group was also administrated with alloxan in a dose of 75 mg/kg through the tails' veins. Twenty-four hours after the administration, blood was gathered under etherization from the descending arotae to measure the concentrations of blood sugar and ketone body in plasma with an autoanalyzer (Hitachi, Model 705).

TEST REAGENTS

1) Used for the measurement of blood sugar was Glucose HA Test WAKO (put by Wako Junyaku Co., Ltd. on the market).

2) Used for the measurement of acetoacetic acid was Ketone Test A Sanwa (sold by Sanwa Chemical Institute Co., Ltd.).

3) Used for the measurement of $\beta$-hydroxybutyric acid was Ketone Test B Sanwa (sold by Sanwa Chemical Institute Co., Ltd.).

The results are set forth in Table 2, from which it is found that there is a significant difference in all the groups and the present composition $\geq$ sodium phytate.

TABLE 3

| | Dose as phytic acid in mg/kg | Sugar in mg/dl | Aceto-acetic acid | Hydroxy-butyric acid |
|---|---|---|---|---|
| Normal Group | | 189 | 0 | 114 |
| Control Group | | 548 ± 46 | 44 | 635 |
| Test Group (1) | 50 mg | 289 ± 38 | 6 | 189 |
| (Present Composition) | 100 mg | 165 ± 72 | 0 | 131 |
| Test Group (2) | 50 mg | 309 ± 68 | 5 | 191 |
| (Na salt) | 100 mg | 182 ± 64 | 4 | 162 |

EXPERIMENT 7

Inhibition of Propagation of Fat Cells of Mice

Skin cells of a mouse just after birth were collected after decapitation, and a liquid medium was added thereto for 2-day culture in a Schale (a laboratory dish). On the third day, an additional liquid medium was provided and, at the same time, the present composition was added to a test group at a concentration of 100 µg/ml to observe under a microscope changes in the skin and fat cells on the daily base from the third day after culture.

From the results, it has been found that the fat cells of the control group show an increase in the amount of fat, but the fat cells of the test group tend to decrease in the amount of fat. In both the test and control groups, any change in the skin cells is not found, which means that the the toxicity of sodium phytate makes no contribution to the reduction in the fat cells.

EXPERIMENT 8

Remediation of Lipometabolism

In a range of 1 to 30 mg calculated as phytic acid, the present composition was administered under anesthesia to four groups of Wistar rats weighing 190 to 200 g and fasted for 12 hours or longer. Five minutes after the administration, blood was gathered from the descending arotae. Sodium citrate was added to the collected blood to regulate its final concentration to 3 mg/ml, which was in turn centrifuged to obtain plasma.

The activity of LPL in the obtained plasma was determined by the measurement of librating fatty acids.

The amount of free fatty acids were measured with NEFAC Test Wako-Kit (put by Wako Junyaku Co., Ltd. on the market).

By measurement, it has been found that the free fatty acids are induced depending upon the amount of sodium phytate in the range of 1 to 30 mg/kg/weight.

With an intravenous injection of an dose of 10 mg/kg/weight, the maximum induction of LPL occurred five minutes after the injection, and was sustained over about 40 minutes.

From the foregoing results, it has been found that the present composition is effective to reduce lipometabolism.

EXPERIMENT 9

Curative Effect on Hepatopathy Models of Rats Induced by Carbon Tetrachloride One (1) mg/kg of carbon tetrachloride was administered to a male rat weighing about 200 g twice a week over ten weeks to induce hepatopathy. How much the hepatopaty was cured was determined in conventional manners by the measurement of the eluting enzymes GOT and GPT due to hepatic cytoclasis to calculate the therapeutic index.

After the inducement of hepatopathy, the present composition set forth in Ex. 10 (5 mg/kg, calcuated as phytic acid) was continuously administered to a group of five rats by the intraperitoneal route for 14 days (physiological saline was administered to a control group) to collect blood from the caudal veins for the measurement of GOT and GPT. As a consequence, a 50% or more increase in the therapeutic index was found.

EXPERIMENT 10

Action upon Mouse's Amnesia

Due to its promoted erythrocytic oxygen dissociation function, phytic acid is expected to produce a defensive effect upon various disorders. Such a defensive effect was studied with a dysmnesia model induced by the loading of a carbon dioxide gas.

EXPERIMENTAL PROCEDURES

The indication used was a single passive avoidance reaction.

1) Acquisition Trial

An animal was placed in a bright chamber of a bright and dark box (comprising a bright chamber and a dark chamber, both being of 15.0×17.5×18.5 cm and including an inlet/outlet combination of 6.0×6.0 cm to measure the length of time by the time when the animal walked into the dark chamber (the reaction potential time during acquisition, hereinafter abbreviated as A.T.). From just after the animal walked into the dark chamber, foot shocks of 2.5 mA were continuously applied to the animal through a floor's grid with a shock generator scrambler, manufactured by Astech Co., Ltd., until the animal again walked into the bright chamber. To confirm that the model was obtained, no foot shock was applied to a control group (no-FS+hypoxia).

2) Retention Trial

After 24 hours of the acquisition trial, the animal was again placed in the bright chamber of the bright/dark box to measure the length of time by the time when the animal walked into the dark chamber (the reaction potential time during the retention trial, hereinafter abbreviated as R.T.).

3) Preparation of Dysmnesia Model

Immediately after the acquisition trial, the animal was placed in a desiccator of 19 cm in diameter and 20 cm in height, and a $CO_2$ gas was then injected into the desiccator for 40 to 45 seconds till apnoea. After the animal was removed from the desiccator, artificial aspiration was immediately tried thereon. The animal was then put back in a home cage. For the confirmation of the model, no $CO_2$ was injected into a control group (FS+no-hypoxia).

4) Administration of Drug

The drug to be examined was introperitoneally administered to a test group of animals at a dose of 10 ml/kg before 30 minutes or 60 minutes of the acquisition trial, while 10 ml/kg of physiological saline was intraperitoneally administrated to a control group of animals.

5) Statistical Assay

For the animals having R.T. exceeding 360 seconds, the average±the standard deviation was found for each group assuming that R.T. was 360 seconds, and statistical assay was made according to the Student's t-test method. For the animals having R.T. exceeding 360 seconds, on the other hand, the retention % was calculated assuming that the memory was retained, and both-side assay was made according to the Fisher's exact provability method.

RESULTS AND CONSIDERATIONS

The results of the respective groups are set out in Table 3.

Referring to the groups of animals to which phytic acid was administrated before 30 minutes of the acquisition trial, there was no difference in the reaction potential time (A.T.) during the acquisition trial between the control group and the test group to which 50 mg/kg of phytic acid were administrated. However, there was a significant increase in the reaction potential time between the control group and the test groups to which 100 mg/kg and 200 mg/kg of phytic acid were administrated, but that increase was of no significance. Referring on the other hand to the groups to which phytic acid was administrated before 60 minutes of the acquisition trial, there was no difference between the control group and the test groups to which 50 mg/kg, 100 mg/kg and 200 mg/kg of phytic acid were administrated. The FS+no-hypoxia control was 64.8±11.1 seconds, while the no-hypoxia control was 44.5±9.1 seconds. In the groups to which phytic acid was administrated before 30 minutes of the acquisition trial, an increase in A.T. was found at a dose of 100 mg/kg or more but, in the groups to which phytic acid was administrated before 60 minutes, such an increase was not found. After about 30 minutes of the administration, phytic acid had some influence upon the behavior of the animals, but such influence were lost after 60 minutes.

Turning to the groups to which phytic acid was administrated before 30 minutes of the acquisition trial, there was no difference in the reaction potential time (R.T.) during the retention trial between the control group and the test groups to which 50 mg/kg and 100 mg/kg of phytic acid were administrated. Referring to the groups to which phytic acid was administrated before 60 minutes of the retention trial, there was a significant increase ($p < 0.05$) between the control group and the test groups to which 50 mg/kg and 100 mg/kg of phytic acid were administrated, but no difference was found in the test group to which 200 mg/kg of pytic acid were administrated. In the groups to which phytic acid was administrated before 30 minutes, no remediation of dysmnesia was found at any dose. Thus, the influence of phytic acid upon the behavior of the animals during the acquisition trial were considered to take part in R.T. In the groups to which phytic acid was administrated before 60 minutes, noticeable remediation of dysmnesia was found at the dosages of 50 mg/kg and 100 mg/kg, but any remediation of dysmnesia was not found at the dose of 200 mg/kg. This implies that phytic acid acts in the Belshave's form.

Due to its promoted erythrocytic oxygen dissociation function, phytic acid serves to enhance the transfer of oxygen into anoxic regions and so histionic disorders due to anoxia. Indeed, phytic acid was found to have an effect upon the amelioration of dysmnesia. It is thus suggested that the promoted erythrocytic oxygen dissociation function is effective for dysmnesia due to hypoxic disorders.

TABLE 3

Action of Phytic Acid upon Dysmnesia due to the Inhale of Carbon Dioxide

| | Dosage (mg/kg i.p.) | n | A.T.(sec) | R.T. (sec) | R (%) |
|---|---|---|---|---|---|
| Before 30 min | | | | | |
| Control Group | 10 | 15 | 37.5 ± 4.9 | 185.0 ± 26.5 | 13 |
| Test Group | 50 | 18 | 38.5 ± 4.6 | 182.9 ± 25.7 | 22 |
| " | 100 | 20 | 8.78 ± 12.4*** | 205.0 ± 26.1 | 25 |
| " | 200 | 17 | 114.8 ± 22.9** | 136.5 ± 30.3 | 17 |
| Before 60 min | | | | | |
| Control Group | 10 | 28 | 51.8 ± 9.1 | 189.4 ± 19.2 | 17 |
| Test Group | 50 | 24 | 44.6 ± 6.5 | 255.1 ± 19.4* | 33 |
| " | 100 | 26 | 50.5 ± 5.7 | 258.2 ± 20.6* | 38 |
| " | 200 | 23 | 61.3 ± 8.2 | 204.2 ± 23.7 | 21 |
| Foot Shock + | | 14 | 68.4 ± 11.1 | 360.0 ± 0.0*** | 92+++ |

TABLE 3-continued

| Action of Phytic Acid upon Dysmnesia due to the Inhale of Carbon Dioxide | | | | |
|---|---|---|---|---|
| Dosage (mg/kg i.p.) | n | A.T.(sec) | R.T. (sec) | R (%) |
| No-Hypoxia No-Foot Shock + Hypoxia | 13 | 44.5 ± 9.1 | 50.6 ± 19.7*** | 0+++ |

*p < 0.05, p < 0.01, *p < 0.001 vs it's control (Student's t-test), +++p < 0.001 vs its's control (Fisher's exact provability test).

EXPERIMENT 11

Inhibition of Propagation of Fat Cells of Mice

Skin cells of a mouse just after birth were collected after decapitation, and a liquid medium was added thereto for 2-day culture in a Schale (a laboratory dish). On the third day, an additional liquid medium was provided and, at the same time, 100 μg/ml of the present composition—the aqueous ferric citrate solution of phytic acid (50 μg/ml, calculated as phytic acid) was added to a test group at a concentration of 100 μg/ml to observe under a microscope changes in the skin and fat cells on the daily base from the third day after culture.

From the results, it has been found that the fat cells of the control group show an increase in the amount of fat, but the fat cells of the test group tend to decrease in the amount of fat. In both the test and control groups, any change in the skin cells is not found, which means that the the toxicities of pytic acid and ferric citrate make no contribution to the reduction in the fat cells.

EXPERIMENT 12

Action upon Erythrodegeneration of Mice

In order to make clarification on how phytic acid and the present composition, known to have a erythrocytic oxygen dissociation function, acts upon erithrodegeneration, tests were carried out in vitro with the red blood cells of rats according to the filtration pressure method.

EXPERIMENTAL PROCEDURES

Sixty (60) minutes after the intraperitoneal administration of the drug to be examined, the animals were placed in a desiccator (of 19 cm in diameter and 20 cm in height), and a carbon dioxide gas was then injected thereinto to measure the length of time by the time when the animals died. It is noted that after 30 minutes or 60 minutes of administration, the test and control groups, each of four mice, were simultaneously placed in the desiccators.

In the statiscal assay carried out according to the Student's t-test method, the average±the standard deviation was calculated for each group.

An erythrocytic suspension was incubated at 37° C. for 5 minutes and then cooled down to room temperature. With a sustended injector (of the 2 ch type, manufactured by Natsume Seisakusho), the suspension was passed at a rate of 5 ml/min through a Millibore membrane (SMWP 013 00, Lot No. N7BU008, manufactured by Millibore) having an average diameter of 5 μm to record its upstream side pressure on recording paper through a pressure transducer (TP-200TL, manufactured by Nippon Koden).

The filtration pressure was estimated in terms of a pressure increase per min till the lapse of 8 minutes from the commencement of injection, and erythrodegeneration was taken as being influenced when there was a significant difference between the control and test groups, as estimated according to the Student's t-test method.

The composition of Ex. 8 and phytic acid (in the form of a sodium salt, Lot No. M7K7653, manufactured by Hani Kagaku) was dissolved in physiological saline and regulated to pH 7.0 with hydrochloric acid. Used as the control was physiological saline containing no phytic acid.

TEST RESULTS

1. Action upon Erythrodegeneration

As set out in Table 4, no appreciable filtration pressure drop was found at 1 mM of phytic acid (at the final concentration), but a filtration pressure rise was about one half of that of the control group, indicating a significant (p<0.01) drop.

TABLE 4

| Action of Phytic Acid upon Erythrodegeneration of Mice | | | |
|---|---|---|---|
| Drug | Concentration | n | Filtration Pressure (mmHg/min) |
| Control Group |  | 6 | 12.4 ± 0.6 |
| Phytic Acid | 1 mM | 3 | 10.1 ± 0.3 |
| Present Composition | 1 mM | 3 | 9.6 ± 0.3 |
| Phytic Acid | 5 mM | 3 | 6.0 ± 0.6 |
| Present Composition | 5 mM | 3 | 5.0 ± 0.3 |

What is claimed is:

1. A highly water-soluble dosage form of phytic acid containing phytic acid, ferric ions and carboxylate ions in a molar ratio of about 10:1:1 to about 1:12:36 of phytic acid: ferric ions: carboxylate ions.

2. A dosage form according to claim 1 additionally containing a saccharide, an amino acid or salt thereof, or an organophosphoric acid or salt thereof.

3. In a method for the oral administration of phytic acid, the improvement which comprises administering the phytic acid in combination with ferric ions and carboxylate ions, said combination having a molar ratio of about 10:1:1 to about 1:12:36 of phytic acid: ferric ions: carboxylate ions.

4. A method according to claim 3, wherein the combination of phytic acid, ferric ion and carboxylate ion also contains a saccharide, an amino acid or salt thereof, or an organophosphoric acid or salt thereof.

* * * * *